(12) United States Patent
Feimer et al.

(10) Patent No.: US 8,701,470 B2
(45) Date of Patent: Apr. 22, 2014

(54) METHOD AND SYSTEM FOR DETERMINING PARTICLE SIZE DISTRIBUTION AND FILTERABLE SOLIDS IN A BITUMEN-CONTAINING FLUID

(75) Inventors: Joseph L. Feimer, Bright's Grove (CA); Ken N. Sury, Calgary (CA)

(73) Assignee: ExxonMobil Upstream Research Company, Houston, TX (US)

( * ) Notice: Subject to any disclaimer, the term of this patent is extended or adjusted under 35 U.S.C. 154(b) by 362 days.

(21) Appl. No.: 13/132,865

(22) PCT Filed: Dec. 7, 2009

(86) PCT No.: PCT/US2009/067009
§ 371 (c)(1),
(2), (4) Date: Jun. 3, 2011

(87) PCT Pub. No.: WO2010/085296
PCT Pub. Date: Jul. 29, 2010

(65) Prior Publication Data
US 2011/0265558 A1 Nov. 3, 2011

(30) Foreign Application Priority Data

Jan. 23, 2009 (CA) .................................. 2650750

(51) Int. Cl.
*G01N 15/06* (2006.01)

(52) U.S. Cl.
USPC ..................... 73/61.75; 73/61.71; 208/390

(58) Field of Classification Search
USPC ........................................................ 73/61.75
See application file for complete search history.

(56) References Cited

U.S. PATENT DOCUMENTS

| | | | |
|---|---|---|---|
| 4,676,889 A | 6/1987 | Hsieh et al. | |
| 4,804,459 A * | 2/1989 | Bartholic et al. | 208/253 |
| 4,818,373 A * | 4/1989 | Bartholic et al. | 208/252 |

(Continued)

FOREIGN PATENT DOCUMENTS

| | | |
|---|---|---|
| CA | 940853 | 1/1974 |
| CA | 2075108 | 1/1994 |

(Continued)

OTHER PUBLICATIONS

Ferworn Kevin A. et al. "Measurement of Asphaltene Particle Size Distributions in Crude Oils Diluted with n-Heptane". Ind. Eng. Chem. Res. 1993,32, 955-959.*

(Continued)

*Primary Examiner* — Hezron E Williams
*Assistant Examiner* — Mark A Shabman
(74) *Attorney, Agent, or Firm* — ExxonMobil Upstream Research Company—Law Department

(57) ABSTRACT

A method and system for determining particle size distribution and/or filterable solids in bitumen-containing fluid is described. A sample of bitumen-containing fluid, such as bitumen-froth feed, bitumen-froth solvent or paraffinic-froth-treated (PFT) bitumen-solvent is obtained. An optimized diluent combination is determined, comprising an aromatic or cycloaliphatic solvent such as toluene, benzene, naphthalene, xylene, anthracene, or cyclohexane together with a C3 to C12 paraffinic solvent. The combination is considered optimized when diluting the sample with the combination maintains substantially the same level of deasphalting in the diluted sample as in the undiluted sample. Upon dilution of the sample with optimized diluent combination, particle size distribution can be accurately determined using optical instrumentation, laser diffraction instrumentation, electrical counting instrumentation, or ultrasonic instrumentation.

15 Claims, 4 Drawing Sheets

(56) References Cited

U.S. PATENT DOCUMENTS

| | | | |
|---|---|---|---|
| 5,143,598 A * | 9/1992 | Graham et al. | 208/390 |
| 5,236,577 A | 8/1993 | Tipman et al. | |
| 5,876,592 A | 3/1999 | Tipman et al. | |
| 5,968,349 A | 10/1999 | Duyvesteyn et al. | |
| 6,007,709 A | 12/1999 | Duyvesteyn et al. | |
| 6,074,558 A | 6/2000 | Duyvesteyn et al. | |
| 6,211,956 B1 * | 4/2001 | Nicoli | 356/337 |
| 6,214,213 B1 * | 4/2001 | Tipman et al. | 208/390 |
| 6,358,403 B1 | 3/2002 | Brown et al. | |
| 6,358,404 B1 | 3/2002 | Brown et al. | |
| 6,712,215 B2 | 3/2004 | Scheybeler | |
| 6,800,116 B2 | 10/2004 | Stevens et al. | |
| 7,067,811 B2 | 6/2006 | Long et al. | |
| 7,141,162 B2 | 11/2006 | Garner et al. | |
| 7,294,156 B2 * | 11/2007 | Chakrabarty et al. | 44/301 |
| 7,363,973 B2 | 4/2008 | Nenniger et al. | |
| 7,540,951 B2 | 6/2009 | Selmen et al. | |
| 7,867,382 B2 * | 1/2011 | Droughton | 208/306 |
| 2005/0150844 A1 | 7/2005 | Hyndman et al. | |
| 2005/0263437 A1 | 12/2005 | Howdeshell | |
| 2006/0113218 A1 | 6/2006 | Hart et al. | |
| 2006/0138036 A1 | 6/2006 | Garner et al. | |
| 2006/0138055 A1 | 6/2006 | Garner et al. | |
| 2006/0144754 A1 | 7/2006 | Van Den Bosch et al. | |
| 2006/0260980 A1 | 11/2006 | Yeung | |
| 2007/0111903 A1 | 5/2007 | Engel et al. | |
| 2009/0200210 A1 * | 8/2009 | Hommema | 208/391 |
| 2010/0258265 A1 * | 10/2010 | Karanikas et al. | 165/45 |

FOREIGN PATENT DOCUMENTS

| | | |
|---|---|---|
| CA | 2200899 | 9/1998 |
| CA | 2232929 | 9/1998 |
| CA | 2353109 | 1/2003 |
| CA | 2471048 | 3/2004 |
| CA | 2527058 | 3/2004 |
| CA | 2505411 | 7/2004 |
| CA | 2425840 | 10/2004 |
| CA | 2435113 | 1/2005 |
| CA | 2493677 | 6/2005 |
| CA | 2454942 | 7/2005 |
| CA | 2455011 | 7/2005 |
| CA | 2726122 | 7/2005 |
| CA | 2750837 | 7/2005 |
| CA | 2750845 | 7/2005 |
| CA | 2750934 | 7/2005 |
| CA | 2750936 | 7/2005 |
| CA | 2750995 | 7/2005 |
| CA | 2751587 | 7/2005 |
| CA | 2751773 | 7/2005 |
| CA | 2799354 | 7/2005 |
| CA | 2799400 | 7/2005 |
| CA | 2799739 | 7/2005 |
| CA | 2750939 | 8/2005 |
| CA | 2520943 | 4/2006 |
| CA | 2490734 | 6/2006 |
| CA | 2502329 | 9/2006 |
| CA | 2538464 | 9/2006 |
| CA | 2521248 | 3/2007 |
| CA | 2612791 | 5/2008 |
| CA | 2714735 | 7/2011 |
| CA | 2729457 | 7/2011 |
| CA | 2733862 | 7/2011 |
| CA | 2806588 | 7/2011 |
| CA | 2806891 | 7/2011 |
| CA | 2719874 | 5/2012 |
| CA | 2733332 | 8/2012 |
| CA | 2735311 | 9/2012 |
| CA | 2736082 | 9/2012 |
| CA | 2737410 | 10/2012 |
| CA | 2738700 | 10/2012 |
| CA | 2805804 | 10/2012 |
| CA | 2815785 | 10/2012 |
| CA | 2739667 | 11/2012 |
| CA | 2740823 | 11/2012 |
| CA | 2740935 | 11/2012 |
| WO | WO99/33936 | 7/1999 |

OTHER PUBLICATIONS

Ferworn, K.A. et al., (1993) "Measurement of Asphaltene Agglomeration form Cold Lake Bitumen Diluted with n-Alkanes", *The Canadian Journal of Chemical Engineering*, vol. 71, October, p. 699-703.

Syvitski, J.P. (editor) (2007). *Principles, Methods and Application of Particle Size Analysis*. Cambridge University Press. ISBN-13: 9780521044615; Chapter 1, pp. 13 to 17 and Chapter 6, pp. 76 to 86.

Wiehe, I.A. et al., (2000) "The Oil Compatibility Model and Crude Oil Incompatibility" *Energy & Fuels*, 14: 56-59.

Wiehe, I.A. et al., (2000) "Application of the Oil Compatibility Model to Refinery Streams" *Energy & Fuels*, 14: 60-63.

International Search Report for PCT/US09/67009 Feb. 5, 2010.

ASTM-D4807 (2010).

\* cited by examiner

METHOD AND SYSTEM FOR DETERMINING PARTICLE SIZE DISTRIBUTION AND FILTERABLE SOLIDS IN A BITUMEN-CONTAINING FLUID

CROSS-REFERENCE TO RELATED APPLICATION

This application is the National Stage of International Application No. PCT/US2009/067009, filed 7 Dec. 2009, which claims priority from Canadian Patent Application 2,650,750 filed Jan. 23, 2009 entitled METHOD AND SYSTEM FOR DETERMINING PARTICLE SIZE DISTRIBUTION AND FILTERABLE SOLIDS IN A BITUMEN-CONTAINING FLUID, the entirety of which is incorporated by reference herein.

FIELD OF THE INVENTION

The present invention relates to methods of and systems for measuring particle size distribution and filterable solids in a bitumen-containing fluid, such as in bitumen-froth or bitumen-solvent mixtures.

BACKGROUND OF THE INVENTION

The demand for heavy crudes such as those extracted from oil sands has increased significantly in order to replace the declining reserves of conventional crude. These heavy hydrocarbons, however, are typically located in geographical regions far removed from existing refineries. Consequently, the heavy hydrocarbons must be transported via pipelines to the refineries. In order to transport the heavy crudes in pipelines to existing refineries they must meet pipeline and refinery specifications. The solids content/level in the transported hydrocarbons must not exceed set specifications. For example, the pipeline specification for basic sediment and water (BS&W) is a maximum of 5000 wppm. The refinery specification for filterable solids is a maximum of 300 wppm which is more stringent than the pipeline specification.

Mineable oil sands contain bitumen, water and mineral matter. Upgrading or partial upgrading to remove water, mineral matter, and some of the asphaltenes contained in bitumen is required to meet pipeline and refinery specifications cited above prior to transport and further processing. Measurement of solids content in bitumen-froth, bitumen-froth solvent mixtures, bitumen-solvent mixtures and bitumen formed during the upgrading process is an important aspect of process control to meet pipeline and refinery specifications. The composition of an oil sand can vary from region to region, as well as within a region. Continuous monitoring and adjustment of the upgrading process is warranted to ensure the product falls within the specifications.

Upgrading units and partial upgrading units located proximal to the oil sands generally employ a two-step process of extraction and separation prior to pipeline transport.

In the extraction step air and chemicals may be added to a bitumen/water/sand slurry to help separate bitumen from the bulk of the sand, clay and other mineral matter. The bitumen attaches to the air bubbles and rises to the top of the separator to form a bitumen-rich froth containing residual solids and water as impurities while the majority of solids settle to the bottom. Paraffinic or other solvent is added to the bitumen-froth and the mixture is pumped to another separation vessel (froth separation unit or FSU). The addition of paraffinic solvents such as propane, butane, pentane etc. promote the precipitation of asphaltenes in the froth separation unit and helps to remove the residual solids and water impurities that readily settle and resulting in a dry bitumen product that meet specifications cited earlier. When a paraffinic solvent is used in froth separation, the product is referred to as a paraffinic froth-treated bitumen (PFT bitumen). The degree of deasphalting can be controlled by the temperature, type and amount of solvent used in the froth separation unit. A high temperature paraffinic froth-treatment (70-90° C.) improves the performance, for example increases the settling rate of the precipitated solids compared to lower temperature operations.

The partial upgrading process targets removal/precipitation of about 50% of the asphaltenes prior to pipeline transport. A partially upgraded product can be blended with either condensate or synthetic crude oil to meet the pipeline viscosity and density specifications. The total filterable solids in the blended product must be less than 300 wppm to meet refinery specifications. Filterable solids as measured by ASTM-D4807 is a key specification which limits the design and operation envelop of the upgrading unit.

The filterable solids content of a deasphalted bitumen product plays a significant role in the design and operation of the froth separation unit and the upgrading unit as a whole. Conventional methodologies such as cited in ASTM D4807 to analyze the filterable solids require hours to complete. A time lag on the order of four to six hours may be experienced between obtaining a sample and completing a measurement. Thus, should an undesirable measurement be noted, four to six hours of potential off-spec production would have occurred prior to adjustment or shut-down of the upgrading unit.

Filterable solids concentrations can be determined from particle size distribution and particle count measurements. Methods to effectively measure the particle size distribution of the solids in bitumen froth and bitumen-solvent mixtures provide important feedback on the operation of the unit and thereby minimize or eliminate upsets, unplanned unit shut downs, and production of off-spec product. A variety of techniques are available for determining a particle size distribution and particle count measurements. Such techniques include optical, laser diffraction, electrical counting and ultrasonic instrumentation.

The high concentration of solids and the opaque nature of the bitumen-froth and bitumen-solvent mixtures make it difficult, if not impossible to obtain on-line particle size distribution measurements. In addition, fouling due to the high concentration of solids and asphaltene precipitation can severely impact the operability of these instruments.

Wiehe and Kennedy, in their publications entitled The Oil Compatibility Model and Crude Oil Incompatibility (Wiehe et al., Energy & Fuels 2000, 14: 56-59); and in Application of the Oil Compatibility Model to Refinery Streams (Wiehe et al., Energy & Fuels 2000, 14: 60-63) discuss an oil compatibility model in which solubility and precipitation of asphaltenes from oil is determined on a toluene-heptane scale. The model is used to determine if a crude oil mixture experiences dissolution or precipitation of asphaltenes at different solvent ratios. This parameter has been used to determine correct proportions and order of blending crude oils for desired proportions, and can be used in preventing fouling of equipment due to unexpected precipitation of asphaltenes from a crude oil stream.

A relatively dilute concentration of solids is desirable when determining particle size distribution. Dilution of bitumen-froth and bitumen-solvent streams prior to analysis of particle size distribution is desirable, not only to permit accurate analysis but also to prevent fouling of the instrumentation.

This is especially important for on-line techniques in which periodic or constant sampling is relied upon to provide feedback to an ongoing upgrading process. However, dilution of a bitumen-containing sample usually leads to a change in asphaltene solubility, and consequently to an inaccurate particle size distribution measurement. Dilution of a sample from a bitumen-containing stream using a typical paraffinic solvent would have the effect of either solubilizing or precipitating asphaltenes, thus leading to a lower or higher solids content in the sample than in the stream. There remains the conundrum that measurement of particle size distribution is best conducted with a diluted sample, but diluting the sample alters asphaltene solubility.

It is, therefore, desirable to provide a method to effectively measure the particle size distribution of the solids in bitumen froth, bitumen froth-solvent mixtures and bitumen-solvent mixtures. Either the particle size distribution and or solids content derived from the same would then assist in providing feedback on the operation of the upgrading unit, thereby minimizing or eliminating upsets, unplanned unit shut downs, or production of off-spec product. Further, such a method could help in optimizing the design of the commercial upgrading processes.

It is desirable to decrease the time-lag between sampling a stream from the upgrading process and obtaining a particle size distribution measurement from the sample.

Further, it is desirable to find a diluent for addition to a bitumen-containing sample that would allow particle size distribution measurements using optical, laser diffraction, electrical counting or ultrasonic techniques without changing the level of deasphalting and fouling.

SUMMARY OF THE INVENTION

It is an object of the present invention to obviate or mitigate at least one or more disadvantages of previous systems or methods for measuring particle size distribution in a bitumen-containing fluid, or of previous methods of preparing a sample for particle size distribution measurement.

In a first aspect, there is provided a method of determining particle size distribution in a bitumen-containing fluid. The method comprises: obtaining a sample of the bitumen-containing fluid; determining an optimized diluent combination comprising an aromatic or cycloaliphatic solvent and a paraffinic solvent, wherein diluting the sample with the optimized diluent combination maintains substantially the same deasphalting as the sample; mixing the sample with the optimized diluent combination to form a diluted sample; and determining particle size distribution in the diluted sample. A particle may be comprised of any combination of mineral solid, water and asphaltene.

In a further aspect, the present invention provides a system for producing from an upgrader a bitumen-solvent having a constant pre-determined filterable solids content. The system comprises: a sampler for obtaining a sample of bitumen-containing fluid from a bitumen-froth stream, bitumen-froth solvent stream, or a PFT-bitumen-solvent stream; means for determining an optimized diluent combination comprising an aromatic or cycloaliphatic solvent and a paraffinic solvent, wherein diluting the sample with the optimized diluent combination maintains substantially the same level of deasphalting as the sample; means for determining particle-size distribution of the sample diluted with the optimized diluent combination; and control means for adjusting a process parameter of the upgrader when the particle size distribution of the sample and the resulting solids content stray from the pre-determined distribution and level respectively.

Advantageously, the fouling propensity of bitumen-froth and bitumen-solvent streams within sampling or analytical instrumentation is substantially reduced if not totally eliminated with this method.

The addition of an optimized diluent combination to a sample of a bitumen-containing fluid reduces the concentration of the solids as well as improves the image resolution using optical methods. Most particle size distribution instruments require low solids concentration. Also, because the fouling propensity of bitumen froth and bitumen-solvent streams is reduced significantly with the use of this method, this method is particularly suited to on-line analysis techniques.

Those skilled in the art can obtain a relationship between the particle size distribution, number of particles in a sample and the filterable solids content. Particle size distribution based on volume using the appropriate density of the particles can be converted to particle size distribution based on weight. The filterable solids content in a sample can be determined using the particle size distribution based on weight in conjunction with the total number of particles in a sample. Most particle size distribution techniques provide both the volume distribution as well as the particle count. The optical technique for determining particle size distributions is well-suited for these measurements.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
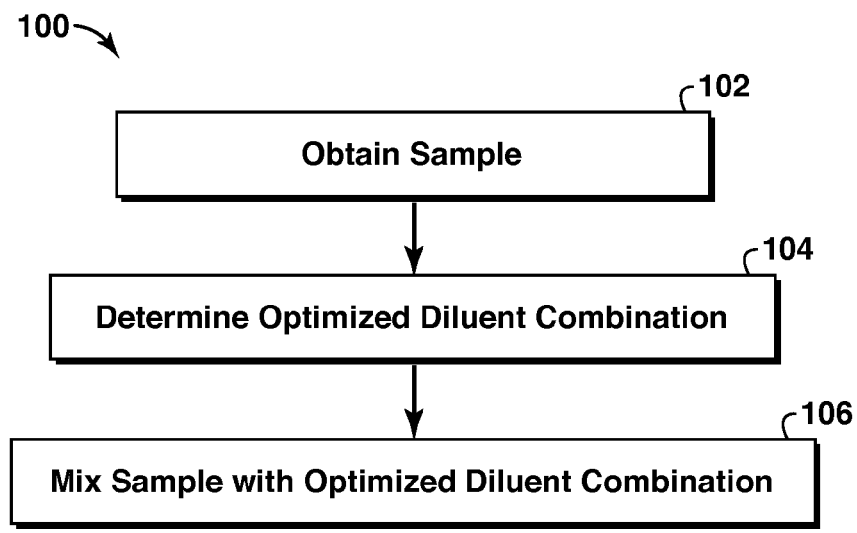
FIG. 1 is a schematic illustration of a method according to an embodiment of the invention.

A method for preparing a bitumen-containing fluid for measurement of particle size distribution is described herein. Further, a method of determining particle size distribution and the calculation of filterable solids content is provided. Also, a system is described for producing, from an upgrader, a bitumen-solvent product having a consistent particle size distribution and filterable solids content. The particle size distribution of the product and filterable solids content can be pre-determined as one appropriate for pipeline standards.

By maintaining "substantially the same level of deasphalting", for example, a C5 asphaltene content determined in the sample and the diluted sample are reasonably comparable to each other so as not to be considered significantly or substantially different. For example, levels that are substantially the same include values that fall within ±5% of the desired value, preferably at least ±2% of the desired value, for example: within ±1% of the desired value.

A "particle", as referred to herein for particle size distribution or particle count measurements, is any combination of mineral solid, water and asphaltene found in the bitumen-containing fluid to be upgraded.

A method described herein allows determination of particle size distribution in a bitumen-containing fluid. The method comprises the steps of obtaining a sample of the bitumen-containing fluid; determining an optimized diluent combination; mixing the sample with the optimized diluent combination; and subsequently determining particle size distribution in the diluted sample. The combination is considered to be optimized because diluting the sample of bitumen-containing fluid with the optimized diluent combination results in a diluted sample that maintains the same level of deasphalting as the undiluted sample.

The step of determining an optimized diluent combination may comprise iterative testing of a sample of the bitumen-containing fluid diluted in solvent combinations ranging from a ratio of 10% to 25% aromatic or cycloaliphatic solvent in paraffinic solvent; and determining the ratio at which substantially the same level of deasphalting is maintained.

The iterative testing may comprise increasing the ratio of aromatic or cycloaliphatic solvent:paraffinic solvent when increased asphaltene precipitation is observed, and decreasing the ratio of aromatic or cycloaliphatic solvent:paraffinic solvent when increased asphaltene solubility is observed.

The particle size distribution may be used further to determine filterable solids content of the bitumen-containing fluid. According to this embodiment, determining an optimized diluent combination involves combining an aromatic or cycloaliphatic solvent with a paraffinic solvent, in the correct quantities so that diluting the sample with the optimized diluent combination maintains the deasphalting level. Specifically, no precipitation or solubilization of asphaltenes occurs in the diluted sample once the optimized diluent combination is mixed with the sample of the bitumen-containing fluid. This allows an accurate determination of particle size distribution.

The bitumen-containing fluid obtained in the method may be a bitumen-froth feed stream, bitumen-froth solvent stream or a PFT-bitumen-solvent stream. "PFT" refers to paraffinic froth treated.

The paraffinic solvent may be linear, branched, or a combination thereof. The paraffinic solvent may be a saturated aliphatic C3 to C12 hydrocarbon. An exemplary type of paraffinic solvent is C5 to C10 hydrocarbon. One specific example of a paraffinic solvent is heptane.

Aromatic or cycloaliphatic solvents that can be used in forming the optimized diluent combination include toluene, benzene, naphthalene, xylene, anthracene, cyclohexane, acetylene, and a combination thereof. By testing combinations of these solvents with the paraffinic solvent selected, a person of skill in the art can arrive at a combination capable of diluting a bitumen-containing fluid without impacting the level of deasphalting. An exemplary aromatic solvent for use in the diluent combination is toluene.

A system for producing a bitumen-solvent product from an upgrader is described. The system permits production of a product having a consistent filterable solids level and/or with a corresponding particle size distribution. The filterable solids target is set by the refinery specification. The system includes a sampler for obtaining a sample, means for determining an optimized diluent combination, means for determining particle size distribution of the sample after dilution, and control means for adjusting a process parameter of the upgrader as necessary to achieve the desired consistent size distribution, or desired filterable solids content. Those skilled in the art can obtain a correlation of the particle size distribution and number of particles in a sample with the filterable solids content. Particle size distribution based on volume using the appropriate density of the particles can be converted to particle size distribution based on weight. The filterable solids content in a sample can be determine using the particle size distribution based on weight in conjunction with the total number of particles in a sample.

In this system, the sampler is one positioned in such a way as to permit sampling of 1) bitumen-froth feed stream (also referred to interchangeably herein as bitumen feed), 2) from bitumen-froth solvent stream or 3) a PFT-bitumen-solvent stream (paraffinic froth treatment)-bitumen solvent. Each such stream may be accessed in an upgrading process.

The means for determining an optimized diluent combination is one that permits evaluation of different combinations of an aromatic or cycloaliphatic solvent with a paraffinic solvent. In the evaluation, the effect of diluting the sample with the optimized diluent combination is assessed to ensure that the same level of deasphalting is maintained between the undiluted sample and the diluted sample. The means for determining particle-size distribution is instrumentation capable of measuring this parameter in the sample after dilution with the optimized diluent combination. The control means is one that permits adjustment of a process parameter of the upgrader as necessary. Such an adjustment may be necessary when the particle-size distribution and filterable solids of the sample stray from the pre-determined values required to meet industry standards.

Figure 5:
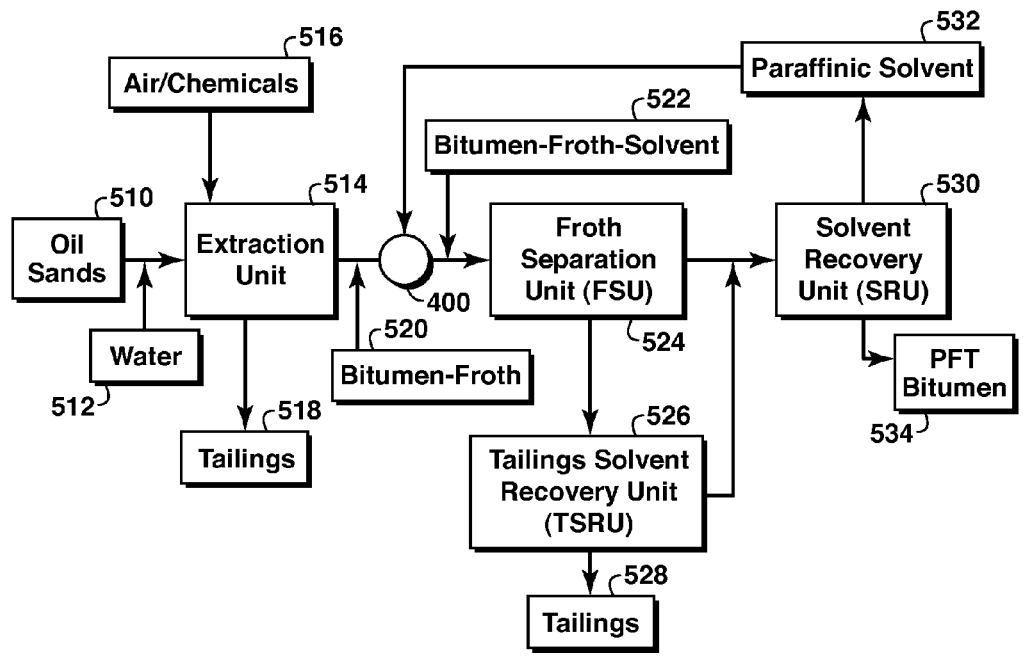
FIG. 5 is a schematic illustration of an oil sands upgrading process incorporating a system according to the invention for maintaining a pre-determined filterable solids concentration.

The term bitumen-containing fluid encompasses any fluid stream containing bitumen that is involved with the upgrading process. This fluid stream may be any bitumen feed stream leading into or out of a froth process. Such a feed stream may include undesirable components yet to be removed, such as sand or water. The fluid may be a bitumen froth sample obtained during or after processing of the fluid in the froth separation unit. An example of a conventional process for upgrading oil sands, which is modified to include the system according to an embodiment of the invention, is illustrated in FIG. 5. The following brief description outlines the conventional process for upgrading oil sands. Oil sand and water are fed to an extraction unit. Air and chemicals may be added to the extraction unit to enhance the separation of bitumen-froth from mineral solids typically referred to as extraction tailings. In the froth separation unit (FSU) a paraffinic solvent is added to precipitate some of the asphaltene and separate out >99% of mineral solids in the bitumen-froth. The paraffinic solvent can be one or more C3 to C12 aliphatic hydrocarbons. A typical solvent used in FSU is a pentane: isopentane mixture. The bitumen-froth solvent stream to FSU may have a solvent-to-bitumen ratio ranging from 1:3 to 10:1, for example. The product from the FSU is a PFT-bitumen-solvent stream. This stream is further along in the upgrading process, relative to the bitumen feed and the bitumen froth, and thus is likely to have fewer solid components to foul and plug the analytical instrumentation.

With respect to the instant invention, an optimized diluent combination is said to be "optimized" because it contains the optimal mix of the primary ingredients: the paraffinic solvent and the aromatic or cycloaliphatic solvent. The optimal combination of these two ingredients in the diluent permits dilution of a sample without substantially changing the level of deasphalting. That is without bringing more asphaltenes into solution or precipitating more asphaltenes out of solution, relative to the undiluted sample. This optimal level is observed to occur at a ratio just prior to precipitation of asphaltenes. Increased solubilization or precipitation of asphaltenes can be observed, for example microscopically or using other techniques, by the disappearance of or increased appearance of solid particles. Excessive aromatic or cycloaliphatic solvent in the combination will have the effect of solubilizing more asphaltenes, while excessive levels of the paraffinic solvent in the combination will have the effect of precipitating more asphaltenes out of the sample. When a balance is achieved, the diluent combination is said to be optimized. Typical ratios of the aromatic or cycloaliphatic solvent to the paraffinic solvent may range from 50% (or 1:1) to 10% (or 1:9). Because the type and quantity of asphaltene found in a bitumen-containing fluid will vary depending on the location from which the bitumen was obtained, as well as other factors, it is prudent to assume that bitumen solubility will change throughout an upgrading process. As the bitumen quality changes, so too does the ratio of the ingredients of the mixture required to maintain the same level of deasphalting when diluting a sample.

Changes in an upgrader may be realized on a day-to-day basis, or can be experienced periodically within a day. Because of this variability, the ability to sample bitumen-containing fluids with periodic regularity and have a rapid analysis of particle size distribution is of great value in the upgrading process.

In the method described, the step of determining an optimized diluent combination may comprise iterative testing of a sample of the bitumen-containing fluid to achieve the optimal ratio. An initial ratio can be used as a starting point. After observations are made regarding precipitation or solubilization of asphaltenes, a subsequent ratio can be selected and evaluated. Although the optimal ratio depends on the solvents used in the optimized diluent combination, ratios ranging from about 10% to 25% of aromatic or cycloaliphatic solvent in paraffinic solvent can be used.

Iterative testing comprises increasing the ratio of aromatic or cycloaliphatic solvent:paraffinic solvent when increased asphaltene precipitation is observed and decreasing the ratio of aromatic or cycloaliphatic solvent:paraffinic solvent when increased asphaltene solubility is observed. This process is repeated while making adjustments to the ratio until neither precipitation nor increased solubility is observed.

Once the optimal ratio of solvents is determined, the level at which a sample will be diluted can be determined. This level may depend on factors such as the estimated solids found in the initial sample. If the initial sample is derived from bitumen feed, the sample may require more dilution with the optimized diluent combination than would a sample of bitumen-solvent obtained after bitumen-froth supernatant has had a paraffinic dilution.

An appropriate dilution with the optimized diluent combination may range from 5:1 to 1000:1 of optimized diluent combination to sample of bitumen-containing fluid. An exemplary range of 10:1 to 100:1 of the optimized diluent combination to the sample is an appropriate range.

In embodiments where particle size distribution is determined, any conventional or state-of-the-art methodology may be used. The method is not restricted to use with a particular instrument or method for determining particle size distribution. This parameter may be evaluated using an optical method, laser diffraction, electrical counting or ultrasonic instrumentation.

In the optical method the particle size distribution is measured using a microscope with a calibrated graticule. A software program is used to determine the size and shape of each particle in a picture and is capable of measuring thousands of particles to obtain a statistically accurate measurement. In the laser diffraction method a laser beam passes through a dispersion of the particles to produce diffracted light. The angle of diffraction increases as the particle size decreases. In electrical counting such as a Coulter counter particles pass through a conductive liquid and generate a pulse. The particle size is dependent on the size of the pulse while the number of particles are determined by counting the number of pulses. In acoustic spectroscopy dispersed particles absorb and scatter ultrasound. The transmitted energy versus frequency is used to determine the particle size.

(Reference; James P M Syvitski (editor) (2007). *Principles, Methods and Application of Particle Size Analysis.* Cambridge University Press. ISBN-13: 9780521044615.

In the system described herein, the sampler for obtaining a sample of bitumen-containing fluid may be positioned at one or more locations in the upgrading process, ranging from bitumen feed and bitumen froth to bitumen-solvent. Sampling at any or all of these locations can occur periodically. More frequent sampling can be conducted from a selected location, for example from a bitumen-solvent, while less frequent sampling could be conducted from alternative locations. The sampler can be of a type allowing diversion of a stream, or one permitting periodic discrete samples to be withdrawn. In an embodiment that involves regular sampling of a bitumen-containing fluid, the sample may be derived from a diverted stream of the upgrading process. An exemplary flow rate of such a diverted stream may be from 10-100 mL per minute. Sampling a fluid without diverting a stream is also encompassed by the methods and systems described herein. An exemplary diverted stream comprises a PFT-bitumen-solvent stream.

The means for determining an optimized diluent combination may encompass a manual or an automated system. An automated instrument for analysis of deasphalting level, that can view microscopic components of a sample and determine precipitation or increased solubilization, may be used. Alternatively, it is a possibility to operate with manual observation of the deasphalting level. The means for determining an optimized diluent combination is one that permits evaluation of both solubilization and precipitation of asphaltenes, in response to which, and adjustment in the solvent ratio is made and tested. Numerous iterations in the ratio change can be made by this means.

The means for determining particle-size distribution of the sample diluted with the optimized diluent combination may be one of the methodologies or instruments described above, with respect to optical instrumentation, laser diffraction instrumentation, electrical counting instrumentation, or ultrasonic instrumentation; or may be any other methodology or instrument capable of making this measurement.

A control means used for adjusting a process parameter may comprise instrumentation permitting mixing of different bitumen feed streams which may have different particle size distribution or filterable solids measurements, in order to achieve the desired level of particle size distribution or filterable solids in the product resulting from the upgrading process.

The system described herein also provides a control means for adjusting a process parameter of the upgrader when the particle size distribution and/or filterable solids content of the upgrader product sample strays from the pre-determined values. Such a control means may include a computerized component in the form of software and/or hardware that notifies when an unexpected or undesirable particle size distribution or filterable solids level is observed. In this way, a process parameter of the upgrader can then be adjusted either in a manual way or in an automated way. If the filterable solids as determined by particle size distribution and the particle count exceeds a specified value, indicative of too many smaller sized particles for the desired specifications, the rate of bitumen feed to the upgrader could then be reduced to increase the settling time in the froth separation unit and allow for the smaller sized solids to settle. Alternatively, a flocculating additive can be injected into the bitumen-forth mixture to increase the settling rate of the solids. Conversely, if the filterable solids level is too low, the bitumen froth feed rate can be increased to the froth separation unit and thereby improve productivity.

Advantageously, the fouling propensity of a bitumen-containing stream, such as a bitumen feed, bitumen-froth or a bitumen-solvent stream is reduced significantly when diluted with the optimized solvent combination. Dilution in a way that avoids clogging of analytical equipment is beneficial to the smooth operation of an upgrading facility. Dilution according to the inventive method has the further advantage of maintaining the same level of deasphalting in the undiluted sample as in the diluted sample. Thus, accurate readings of particle size distribution can be obtained using state-of-the-art methodology in an on-line manner. On-line measurement permits rapid response, should an off-specification reading be detected. Previous methods of sampling and evaluating particle size distribution in bitumen-containing fluids did not permit on-line readings from diluted samples. Samples were instead sent away for laboratory analysis. A number of hours were required to obtain readings. An unexpectedly high or low value would take much more time to detect and correct than the shorter time period achievable using the method of the instant invention.

In one embodiment, an optimum heptane-toluene mixture is added to a bitumen-froth or bitumen-solvent stream such that these streams are diluted without changing the level of deasphalting. The optimum heptane-toluene mixture is found by systematically changing the composition of heptane and toluene to the point just before asphaltene precipitation occurs (sometimes referred to as the toluene equivalence point). A microscope is used to observe the formation of asphaltenes in samples diluted with various heptane-toluene mixtures. The addition of the optimum heptane-toluene mixture reduces the concentration of the solids as well as improves the image resolution using optical methods.

FIG. 1 is a schematic illustration of a method 100 of preparing a bitumen-containing fluid for use in particle size distribution analysis according to an embodiment of the invention. The initial step 102 of obtaining a sample of the bitumen-containing fluid is followed by the step of determining the optimized diluent combination 104. In this step, an aromatic or cycloaliphatic solvent and a paraffinic solvent are combined and optimized so that diluting the sample with the optimized diluent combination maintains substantially the same level of deasphalting as the sample. The step of mixing the sample with the optimized diluent combination 106 allows formation of a diluted sample that can then go on to particle size distribution analysis.

Figure 2A:
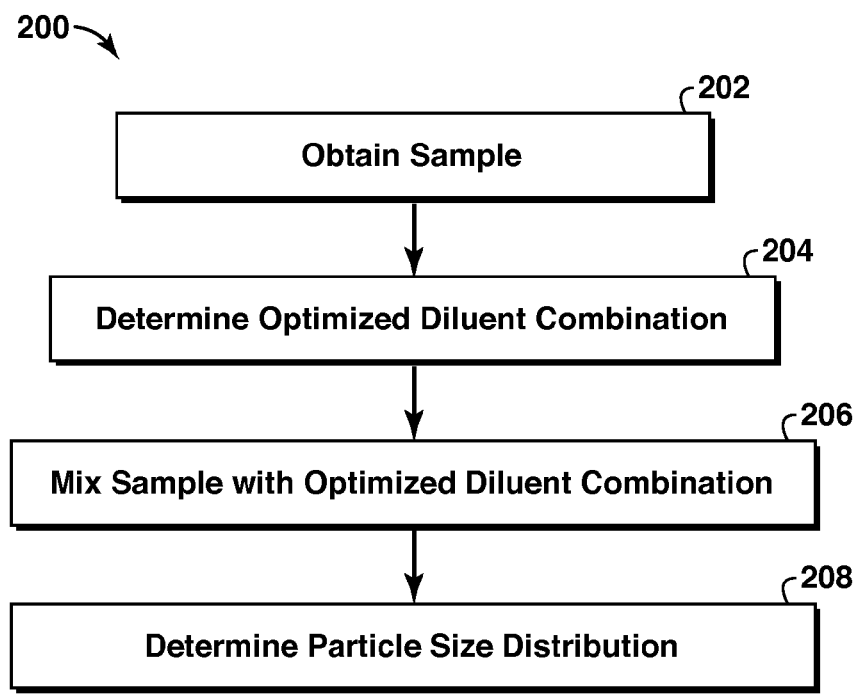
FIG. 2A is a schematic illustration of a method according to a further embodiment of the invention that includes determining particle size distribution.

FIG. 2A is a schematic illustration of a method 200 according to a further embodiment of the invention for determining particle size distribution in a bitumen-containing fluid. The step 202 of obtaining a sample of the bitumen-containing fluid is followed by the step of determining the optimized diluent combination 204. In this step, an aromatic or cycloaliphatic solvent and a paraffinic solvent are combined and optimized so that diluting the sample with the optimized diluent combination maintains substantially the same level of deasphalting as the sample. The step of mixing the sample with the optimized diluent combination 206 forms a diluted sample that proceeds to the step of determining particle size distribution 208.

Figure 2B:
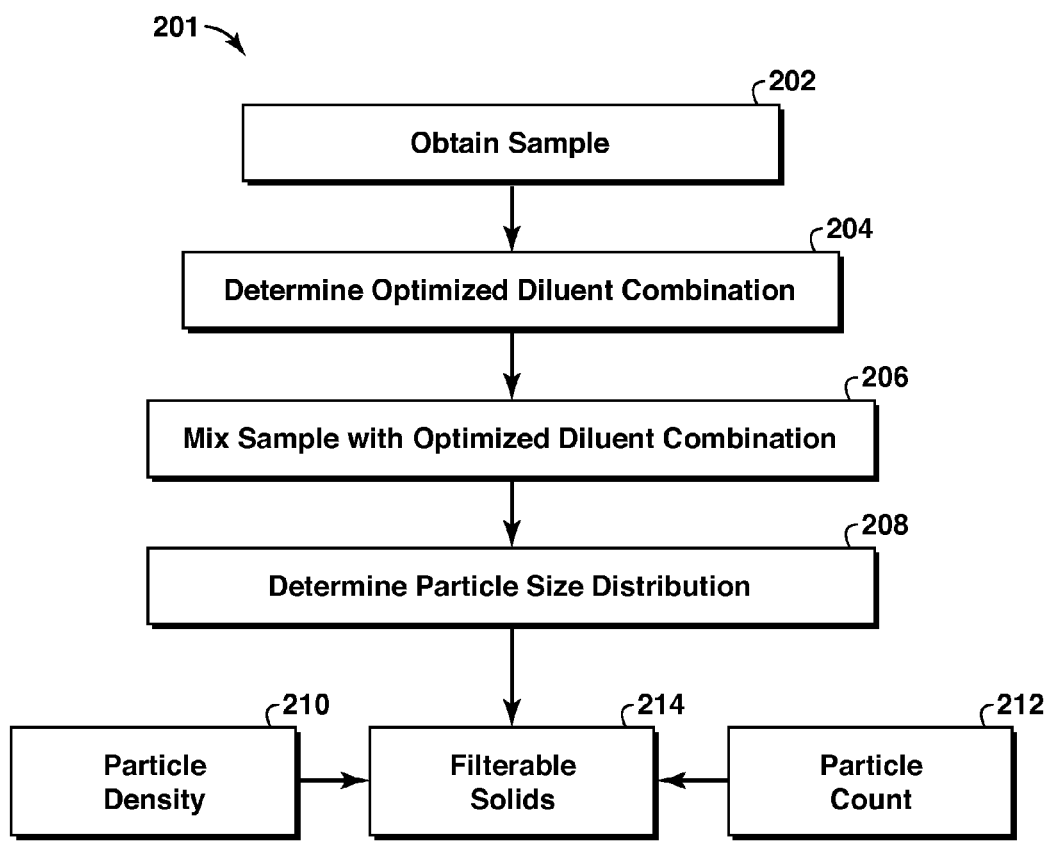
FIG. 2B is a schematic illustration of a method according to a further embodiment of the invention that includes determining filterable solids content.

FIG. 2B is a schematic illustration of a method 201 according to a further embodiment of the invention for determining filterable solids content. This is an extension of the particle size determination in FIG. 2A whereby the particle density 210 is determined and the particle count 212 is determined. These parameters are used together with the particle size distribution 208 to determine the filterable solids content 214.

Figure 3:
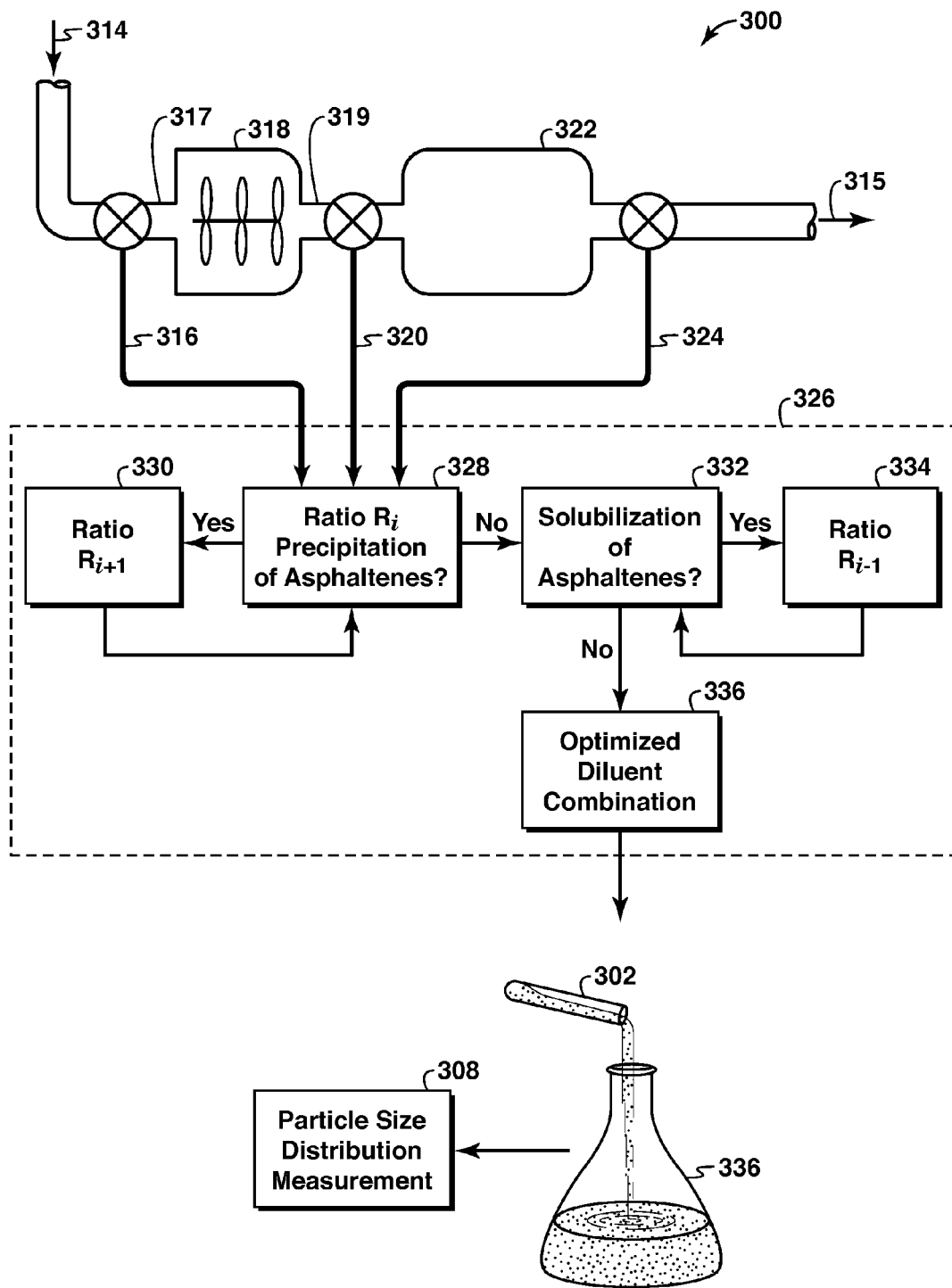
FIG. 3 is a diagrammatic illustration of the iterative testing used according to an embodiment of the invention for determining an optimized diluent combination.

FIG. 3 is a diagrammatic illustration of a system 300 involving iterative testing used for determining an optimized diluent combination. A bitumen-containing feed 314 moves through the upgrading process to form an upgraded product 315 for pipeline transport. A bitumen-froth feed sample 316 may be taken for assessment according to the invention, or may be directed through a conduit 317 to be mixed in an upgrading process. A paraffinic solvent is added to the bitumen froth and mixed in a static mixer 318 to form a bitumen-froth-solvent mixture 319. A bitumen-froth-solvent sample 320 may be taken for assessment according to the invention. A froth separation unit, 322 is used to separate out the mineral matter, water and asphaltenes. A PFT-bitumen-solvent sample 324 may then be taken for assessment according to the invention. At any given time, one of the bitumen-froth feed sample 316, the bitumen-froth-solvent sample 320 and/or the PFT bitumen-solvent sample 324 may be assessed to determine an optimized diluent combination comprising an aromatic or cycloaliphatic solvent and a paraffinic solvent. An iterative testing process 326 is used to arrive at an optimized diluent combination 336. Briefly, a sample is first exposed 328 to an initial ratio ($R_i$) of solvents, expressed as aromatic/cycloaliphatic: paraffinic. The sample is assessed for precipitation of asphaltenes. Should asphaltenes precipitate, the sample is tested 330 with a higher ratio ($R_{i+1}$) of solvents and iteratively assessed for precipitation of asphaltenes until no asphaltenes precipitate.

Solubilization of asphaltenes is also observed 332 within a diluted sample, and optimization is undertaken to ensure that the ratio of solvents is not one that solublizes more asphaltenes into solution. If asphaltenes are increasingly solubilized when a sample is diluted, the sample is tested 334 with a lower ratio of solvent ($R_{i-1}$) to achieve a level at which the deasphalting level of the sample is maintained in the diluted sample, referred to as the optimized diluent combination 336. An appropriate adjustment in solvent ratio can readily be determined by a person of skill in the art.

The terms $R_{i+1}$ and $R_{i-1}$ are illustrative of an increase or decrease in the solvent ratio, but are not limited to a particular increment. Whether $R_i$ is increased or decreased by more or less than one percent per iteration is a decision easily made by a person of skill in the art. For example, there may be reason to believe that in the interests of minimizing the number of iterations, a large change in solvent ratio is warranted. Further, minor incremental adjustments of less than one percent may be of value in achieving the optimized diluent combination.

The bitumen-containing fluid sample 302, is then combined with the optimized diluent combination 336, and is forwarded to instrumentation capable of particle size distribution measurement 308. Optionally, filterable solids may be determined on the basis of the particle size distribution measurement, in a manner consistent with the method shown in FIG. 2B.

Figure 4:
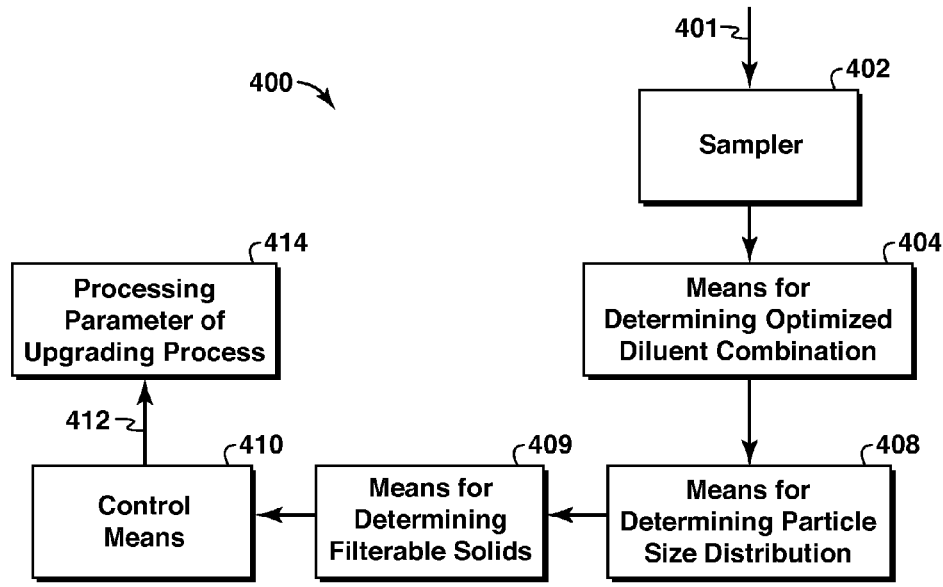
FIG. 4 is a schematic illustration of a system according to an embodiment of the invention.

FIG. 4 is a schematic illustration of a system 400 for producing from an upgrading process a bitumen-solvent having a constant pre-determined filterable solids concentration. A sampler 402 is provided for obtaining a sample of bitumen-containing fluid 401 from bitumen-froth, bitumen-froth solvent, or PFT bitumen-solvent in an upgrading process.

A means for determining an optimized diluent combination 404 is illustrated in this system. A means for determining particle size distribution 408 of the sample diluted with the optimized diluent combination is provided, and a means of determining the filterable solids 409 based on the particle size distribution 408 is also included. A control means 410 is shown, for sending a message 412 to adjust a processing parameter 414 of the upgrading process when the particle size distribution and/or filterable solids content of the sample of bitumen containing fluid 401 strays from a pre-determined values.

FIG. 5 is a schematic illustration of an oil sands upgrading process that includes a system 400 according to an embodiment of the instant invention, for maintaining a pre-determined filterable solids concentration. Bitumen obtained from oil sands 510 is combined with water 512 and delivered to an extraction unit 514 where exposure to air and/or chemicals 516 occurs. Tailing 518 are removed. Bitumen-froth 520 flowing from the extraction unit is then assessed by the system 400 according to an embodiment of the invention to determine whether iterative adjustments are required in order to maintain a constant pre-determined filterable solids concentration, and if necessary, adjustments are made. The resulting bitumen-froth-solvent 522 is forwarded to the froth separation unit 524, and the tailings solvent recovery unit 526 receiving tailings derived from the froth separation unit, is used to separate tailings 528 from recoverable solvent, which is then forwarded to the solvent recovery unit 530. Paraffinic solvent 532 recovered from the solvent recovery unit 530 can thus be re-used in the system. Ultimately, an upgraded product of PFT bitumen 534 is formed in the process.

The system 400 depicted in this embodiment derives bitumen-containing fluid from a bitumen-froth feed stream. However, it is understood that the system may be used to test samples derived from other stages of the upgrading process, for example from a bitumen-froth solvent stream, or from a PFT-bitumen-solvent stream. Fluids from any or all of these stages may be tested in the upgrading process, as desired.

Detailed embodiments of the invention are described in the examples below.

EXAMPLES

Example 1

Optimizing Dilution of a Kearl Bitumen-Solvent Sample for Particle Size Distribution Measurement Oil sand was obtained from Kearl Oil Leases in Alberta. A Kearl bitumen-solvent was prepared as follows. Kearl bitumen-froth (177 grams) was added to a 600 ml autoclave and heated to 70° C. A pentane:isopentane solvent mixture (270 ml of 60:40 wt %) was added to the heated Kearl bitumen-froth in the 600 ml autoclave and stirred at 500 rpm for 20 minutes. The solvent-to-bitumen weight ratio was 1.6 (specifically, 1.6:1). After 20 minutes the stirrer was shut off and the solids where allowed to settle for 60 minutes. After 60 minutes the supernatant was removed for further testing.

Toluene (2 ml) and heptane (16 ml), forming an 11 vol % toluene-in-heptane solution, were mixed in a 50 ml sample vial. Kearl bitumen-solvent supernatant (5 ml of 1.6 ratio), prepared as described above, was added to the 11 vol % toluene-in-heptane solution and agitated. One drop of the agitated solution was added to a glass plate. A microscope was used to observe the formation of asphaltenes. Numerous precipitated asphaltene particles were observed microscopically.

Toluene (4 ml) and heptane (14 ml), forming a 22 vol % toluene-in-heptane solution, were mixed in a 50 ml sample vial. Kearl bitumen-solvent supernatant (5 ml of 1.6 ratio, as prepared above) was added to the 22 vol % toluene-in-heptane solution and agitated. One drop of the agitated solution was added to a glass plate. A microscope was used to observe the formation of asphaltenes. Although some mineral matter was detected, there were no asphaltene particles observed, indicating a solubilization of asphaltenes.

Further microscopic observations of the Kearl bitumen-solvent mixture diluted with different levels of vol % toluene-in-heptane solution were made. The optimum heptane-toluene mixture was determined by systematically changing the composition of heptane and toluene to the level just before asphaltene precipitation occurs. This may be referred to as the toluene equivalence point. For the Kearl bitumen-solvent mixture prepared in this example, the optimum heptane-toluene mixture was determined to be 15 vol % toluene and 85% vol % heptane, or 15 vol % toluene-in-heptane.

Example 2

Optimizing Dilution of An Athabasca Mining Lease Bitumen-Solvent Sample for Particle Size Distribution Measurement An Athabasca Mining Lease bitumen-solvent (also termed as Athabasca bitumen-solvent) was prepared as follows. Athabasca bitumen-froth (177 grams) was added to a 600 ml autoclave and heated to 70° C. A pentane:isopentane solvent mixture (270 ml of 60:40 wt %) was added to the heated Athabasca bitumen-froth in the 600 ml autoclave and stirred at 500 rpm for 20 minutes. The solvent-to-bitumen weight ratio was 1.6. After 20 minutes the stirrer was shut off and the solids where allowed to settle for 60 minutes. After 60 minutes the supernatant was removed for further testing.

Iterative observations of the Athabasca bitumen-solvent mixture diluted with different levels of vol % toluene-in-heptane solution were made. The optimum heptane-toluene mixture was determined by systematically changing the composition of heptane and toluene to the level just before asphaltene precipitation occurs. The optimum toluene-heptane mixture for the supernatant was determined following the same method described above for the Kearl bitumen sample in Example 1. For the Athabasca bitumen-solvent mixture, the optimum heptane-toluene mixture was determined to be 15 vol % toluene and 85% vol % heptane.

Example 3

Optical Image Analysis of Particle Size in Bitumen-Froth

Athabasca bitumen-froth (20 grams) was heated to 70° C. in a 600 ml autoclave. A pentane:isopentane (or "C5") mixture (30 ml of 60:40 wt %) was added to the heated bitumen-froth in the 600 ml autoclave and stirred at 500 rpm for 20 minutes. The C5:bitumen weight ratio was 1.6. A mixture of 15 vol % toluene and 85 vol % heptane (450 mL) was added to the Athabasca bitumen froth-solvent solution and mixed at 70° C. and 500 rpm for 2 minutes. The bitumen-froth sample was diluted 10:1. The C5 asphaltene content was determined on a supernatant sample collected from the 600 ml autoclave.

The C5 asphaltene level in the supernatant was found to be 9.2 wt % which is similar to the expected asphaltene in a 1.6 C5:bitumen at 70° C. These data indicate that the optimum 15% toluene-heptane mixture did not affect the level of deasphalting. Images of solids in supernatant were obtained using a Canty On-line Optical Particle Analyzer. A 10:1 dilution of the C5-bitumen in the optimum toluene-heptane solution significantly reduced the concentration of solids and allowed enough light to penetrate so that the image analysis software could resolve the particles and determine the particle size distribution.

In the preceding description, for purposes of explanation, numerous details are set forth in order to provide a thorough understanding of the embodiments of the invention. However, it will be apparent to one skilled in the art that these specific details are not required in order to practice the invention.

The above-described embodiments of the invention are intended to be examples only. Alterations, modifications and variations can be effected to the particular embodiments by those of skill in the art without departing from the scope of the invention, which is defined solely by the claims appended hereto.

The invention claimed is:

1. A method of determining particle size distribution in a bitumen-containing fluid comprising:
    obtaining a sample of the bitumen-containing fluid;
    determining an optimized diluent combination comprising an aromatic or cycloaliphatic solvent and a paraffinic solvent by diluting the sample with different diluent combinations and selecting the optimized diluent combination, wherein diluting the sample with the optimized diluent combination maintains substantially the same level of deasphalting as the sample;
    mixing the sample with the optimized diluent combination to form a diluted sample, wherein the diluted sample contains at least a 5:1 ratio of the optimized diluent combination to the bitumen-containing fluid; and
    determining particle size distribution in the diluted sample, indicative of particle size distribution of the bitumen-containing fluid.

2. The method of claim 1, wherein the particle size distribution of the diluted sample is used to determine concentration of filterable solids.

3. The method of claim 1, wherein the bitumen-containing fluid comprises a bitumen-froth feed stream, bitumen-froth solvent stream or a PFT-bitumen-solvent stream.

4. The method of claim 3, wherein the bitumen-containing fluid is a PFT-bitumen-solvent stream.

5. The method of claim 1, wherein the paraffinic solvent is linear, branched, or a combination thereof.

6. The method of claim 5, wherein the paraffinic solvent is a saturated aliphatic C3 to C12 hydrocarbon.

7. The method of claim 6, wherein the paraffinic solvent is a C5 to C10 hydrocarbon.

8. The method of claim 7, wherein the paraffinic solvent is heptane.

9. The method of claim 1, wherein the aromatic or cycloaliphatic solvent is toluene, benzene, naphthalene, xylene, anthracene, cyclohexane, acetylene, or a combination thereof.

10. The method of claim 9, wherein the aromatic or cycloaliphatic solvent is toluene.

11. The method of claim 1, wherein the step of determining an optimized diluent combination comprises:
    iterative testing of the sample of the bitumen-containing fluid diluted in solvent combinations ranging from a ratio of 10% to 25% aromatic or cycloaliphatic solvent in paraffinic solvent; and
    determining a ratio at which substantially the same level of deasphalting is maintained.

12. The method of claim 11, wherein iterative testing comprises increasing the ratio of aromatic or cycloaliphatic solvent:paraffinic solvent when increased asphaltene precipitation is observed, and decreasing the ratio of aromatic or cycloaliphatic solvent:paraffinic solvent when increased asphaltene solubility is observed.

13. The method of claim 1, wherein the diluted sample contains from 5:1 to 1000:1 of the optimized diluent combination to the bitumen-containing fluid.

14. The method of claim 13 wherein the diluted sample contains from 10:1 to 100:1 of the optimized diluent combination to the bitumen-containing fluid.

15. The method of claim 1, wherein the particle size distribution is determined using an optical method, laser diffraction, electrical counting or ultrasonic instrumentation.

* * * * *